(12) United States Patent
Pappas

(10) Patent No.: US 6,238,434 B1
(45) Date of Patent: May 29, 2001

(54) KNEE JOINT PROSTHESIS WITH SPINOUT PREVENTION

(75) Inventor: Michael J. Pappas, Caldwell, NJ (US)

(73) Assignee: Biomedical Engineering Trust I, NJ (US)

( * ) Notice: Subject to any disclaimer, the term of this patent is extended or adjusted under 35 U.S.C. 154(b) by 0 days.

(21) Appl. No.: 09/368,782

(22) Filed: Aug. 5, 1999

Related U.S. Application Data

(60) Provisional application No. 60/095,382, filed on Aug. 5, 1998.

(51) Int. Cl.$^7$ ........................................... A61F 2/64
(52) U.S. Cl. .......................... 623/20.29; 623/20; 623/33
(58) Field of Search .................. 623/20.29, 20.15, 623/20.25, 20.33, 20.34

(56) References Cited

U.S. PATENT DOCUMENTS

| | | | |
|---|---|---|---|
| 4,136,405 | * | 1/1979 | Pastrick et al. . |
| 4,568,348 | * | 2/1986 | Johnson et al. . |
| 5,071,438 | * | 12/1991 | Jones et al. . |
| 5,387,240 | * | 2/1995 | Pottenger et al. . |
| 5,951,603 | * | 9/1999 | O'Neil et al. . |

FOREIGN PATENT DOCUMENTS

2707871 * 1/1995 (FR) .

* cited by examiner

Primary Examiner—Bruce Snow
(74) Attorney, Agent, or Firm—Anthony J. Casella; Gerald E. Hespos; Michael J. Porco

(57) ABSTRACT

A knee joint prosthesis is provided. The prosthesis includes a femoral component for mounting to the distal end of a femur, a tibial component for mounting to the resected proximal end of the tibia and a bearing disposed between the femoral and tibial components. The tibial component includes a superior bearing surface with a recess extending distally into the bearing surface. The bearing includes an inferior bearing surface for engagement on the superior bearing surface of the tibial component. Additionally, the bearing includes a projection that is rotatably engaged in the recess of the tibial component. Rotation of the bearing relative to the tibial component is limited by a stop extending from the superior bearing surface of the tibial component. The stop is engaged in a slot formed in the inferior surface of the bearing. The slot is concentric about the rotational axis and extends through an arc consistent with the desired maximum range of rotation. Engagement of the stop in the slot limits rotation and prevents spinout of the knee prosthesis.

13 Claims, 3 Drawing Sheets

KNEE JOINT PROSTHESIS WITH SPINOUT PREVENTION

This application claims priority on Provisional Patent Appl. No. 60/095,382, flied Aug. 5, 1998.

BACKGROUND OF THE INVENTION

1. Field of the Invention

The subject invention relates to orthopedic prosthetic components, and particularly to a knee joint prosthesis.

2. Description of the Related Art

A natural knee joint includes the distal end of the femur, the proximal end of the tibia and a meniscus bearing therebetween. The femur and the tibia are held in proper relationship to one another and to the bearing by a plurality of ligaments, including the posterior cruciate ligament, the anterior cruciate ligament and collateral ligaments. Flexion of the knee joint causes the tibia to rotate relative to the femur about an axis extending generally in a medial-to-lateral direction. Flexion also generates rotation of the tibia about its own axis.

Damage or disease can affect the ability of the natural knee to function properly. The damage or disease can deteriorate the bones, the articular cartilage, the ligaments or some combination thereof. A damaged or diseased natural knee can be replaced by a prosthetic knee joint. A prior art knee joint prosthesis includes a femoral component securely mounted to the distal end of a resected femur, a tibial component securely mounted to the proximal end of a resected tibia and a bearing disposed between the femoral and tibial components. The inferior face of the femoral component includes a pair of condyles. The condyles have a convexly arcuate shape, and the superior surface of the bearing has a pair of arcuate concave regions for articular bearing engagement with the condyles of the femoral component. The superior face of the tibial component may be substantially planar and is in bearing engagement with the inferior face of the bearing.

Currently available prosthetic knee joints take many different forms depending upon the preferences of the orthopedic surgeon, the condition of the natural knee and the health, age and mobility of the patient. Some prior art knee joint prostheses fixedly mount the inferior surface of the bearing to the superior surface of the tibial component. Other knee joint prostheses permit rotary movement and/or sliding movement between the bearing and the tibial component. Movement of the bearing against the tibial component achieves many functional advantages described in the prior art. These functional advantages include an avoidance of dislocation in response to normal walking movement without reliance upon a fixed hinged connection. Very effective prior art knee joint prostheses that incorporate certain of the structural features referred to herein are disclosed in U.S. Pat. No. 4,470,158 and U.S. Pat. No. 4,309,778.

A prior art knee joint that permits rotational movement of the bearing on the tibial component is shown in FIGS. 1–6, and is identified generally by the numeral 100. The prior art prosthesis 100 includes a femoral component 102 for mounting to the distal end 104 of the natural femur 106. The femoral component 102 includes an inferior articular bearing face having medial and lateral condyles 108 and 110 as shown in FIG. 2.

The prior art prosthesis 100 further includes a tibial component 112 that is mounted to the resected proximal end 114 of a tibia 116. The tibial component 112 includes an inferior surface having a generally conical projection 118 configured to be engaged in a cavity prepared in the resected distal end 114 of the tibia 116. The tibial component 112 further include a general planar superior bearing surface 120. The bearing surface 120 is formed with a generally conical central recess.

The prior art knee prosthesis 100 further includes a bearing 122 disposed between the femoral component 102 and the tibial component 112. The prior art bearing includes a superior articular bearing surface 124 configured for articular bearing engagement with the condyles 108 and 110 of the femoral component 102. The bearing 122 further includes an inferior surface for engagement with the tibial component. More particularly, the inferior surface of the prior art bearing 122 includes a central projection (not shown) that is rotatably engaged in the recess that extends into the superior surface 120 of the tibial component 112. The inferior surface of the bearing further includes a generally planar bearing surface 126 that is in rotational bearing engagement on the superior planar bearing surface 120 of the tibial component 112.

The components of a knee joint undergo complex movement relative to one another during walking and other activities. In particular, natural movement of the knee joint causes rotation of the tibia about a generally medial to lateral axis. Simultaneously, the natural movement of the leg will generate some pivotal movement between the tibia and femur about an axis extending generally along the load bearing direction. This pivoting movement will cause some rotation of the prior art bearing 122 on the femoral and tibial components 102 and 112. Rotation of the bearing 122 relative to the femoral component 102 causes the condyles 108 and 110 of the femoral component 102 to climb upwardly toward the lips at the anterior and posterior ends of the bearing 122. This creates the potential for a spinout dislocation. The spinout can be controlled by proper attention to maintenance of collateral ligament tension during implantation. However, the cruciate ligaments are the principle anterior-posterior and medial-lateral stabilizers of the knee. These cruciate ligaments often are removed as part of the surgery to implant the prosthetic knee. Thus, the potential for dislocation exists with prior art knee joint prostheses that employ a rotating bearing.

The instability of the prior art rotating bearing prosthetic knee joint is illustrated most clearly in FIGS. 1–6. In particular, the prior art rotating bearing 122 can be forced to rotate to a dislocated position under the action of combined effects of an anterior-posterior shearing load, distraction of one of the condylar components 108 and 110 of the femoral prosthetic component 102 and a lax collateral ligament associated with the distracted component. Only ligament tension sufficient to prevent the femoral condyle on the distracted side from climbing over the lip of the bearing can prevent such dislocation. There is no other sufficient soft or hard tissue in the knee to prevent such dislocation. The dislocation mode is stable under compressive load. Both anterior-posterior and medial-lateral shift of the prior art femoral component 102 relative to the tibial component 112, as illustrated in FIGS. 5 and 6, must accompany such dislocation. The shearing force and the effect of the vertical rotational axis of the bearing accentuate conditions that can lead to the illustrated spinout. Spinout does not occur in the prior art prosthetic joints where there is an allowance for anterior-posterior translation of the bearing. Thus, the illustrated spinout is a unique disadvantage of a fixed axis rotating platform tibial bearing knee prosthesis as illustrated in FIGS. 1–6.

One prior art technique for minimizing spinout dislocation involves the use of a bearing with increased engagement between the bearing and the femoral component. Such a bearing requires a greater degree of distraction to allow spinout. Although prosthetic knee joints of this type reduce spinout, they do not completely eliminate the occurrence of spinout.

The prior art also includes a rotational stop on the patellar component of the prosthetic knee joint marketed under the name New Jersey LCS. The rotational stop, however, has not prevented spinout of the rotating patella bearing.

In view of the above, it is an object of the subject invention to provide a successful anti-spinout stop joint that will not adversely affect the function of the prosthetic joint.

It is also an object of the subject invention to provide a prosthetic knee joint that can provide enough rotary motion for the needed functions, while still preventing spinout.

SUMMARY OF THE INVENTION

The subject invention is directed to a rotating platform prosthetic knee joint. The prosthetic knee joint includes a femoral component for mounting to a prepared distal end of a femur. The prosthetic component may be of prior art configuration, and includes an inferior articular bearing surface defined by medial and lateral condyles.

The prosthetic joint of the subject invention further includes a tibial component for mounting to the resected end of the tibia. The tibial component may include an inferior projection extending into a cavity prepared in the resected proximal end of the tibia. Additionally, a combination of structural elements and/or bone cement are provided to prevent rotation of the tibial component on the resected proximal end of the tibia. The tibial component may include a recess extending generally centrally into the superior surface thereof. Additionally, a bearing surface may surround the recess. The superior bearing surface of the tibial component may be substantially planar.

The knee prosthesis of the subject invention further includes a bearing disposed between the femoral and tibial components. The bearing may be formed from a non-metallic material and includes a superior surface for articular bearing engagement with the condyles of the femoral component and an inferior bearing surface for rotary bearing engagement with the superior bearing surface of the tibial component. The bearing further includes a projection extending into the recess of the tibial component. The projection and recess cooperate to permit rotation of the bearing on the tibial component, while preventing sliding translation.

The prosthetic joint of the subject invention further includes structure for limiting the range of rotational movement of the bearing on the tibial component. The rotational limitations are provided to prevent excessive rotation that could cause spinout as described above. However, the rotational limitations should provide enough rotary motion for needed function of the knee. Preferably, the prosthetic component is configured to limit the rotary motion only for patients where such limitation appears necessary. Thus, rotational limitations may not be provided on prostheses for patients where it appears that adequate collateral ligament tension can be maintained post-operatively for preventing dislocation. The means for limiting rotation can be slot formed on one of the bearing and tibial components and a projection formed on the other of the bearing and tibial component. For example, the inferior bearing face of the bearing may be formed with a slot defining an arc generated about the axis of rotation of the bearing relative to the tibial component. In this embodiment, the tibial component includes a projection slidably engaged in the slot. The projection may be removably mounted to the tibial component so that the projection is incorporated into the prosthetic joint only for patients that appear to require some form of rotational limitation for preventing spin-out dislocation. The slot may be dimensioned to provide for a total of 90° of axial rotation (+/−45°) which is sufficiently in excess of a required maximum rotation of 80° (+/−40°) needed for most human activities. Thus, normal knee function is substantially unaffected by the prosthesis.

DETAILED DESCRIPTION OF THE PREFERRED EMBODIMENT

Figure 6:
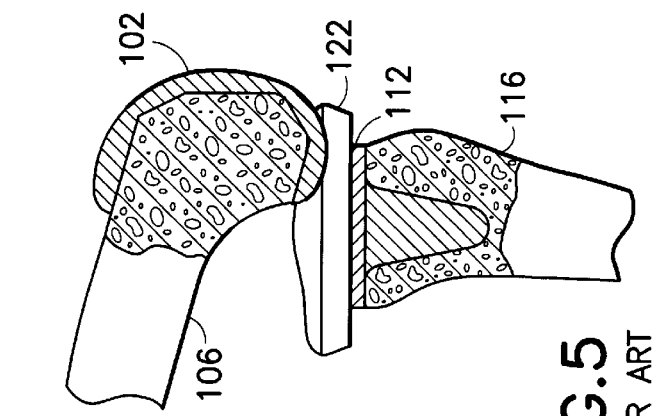
FIG. 6 is a top plan view of the prior art prosthesis as shown in FIG. 5.
Figure 4:
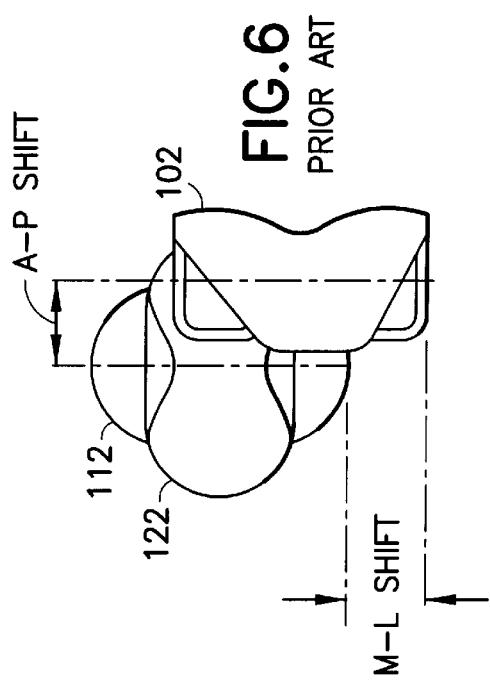
FIG. 4 is a top plan view of the prior art prosthesis as shown in FIG. 3.

A knee prosthesis in accordance with the subject invention is identified generally by the numeral 10 in FIGS. 7–15. The prosthesis 10 includes a femoral component 12 as shown in FIGS. 10–15. The femoral component 12 is substantially the same as the prior art femoral component 102 described and illustrated above. More particularly, the femoral component 12 is mounted to a surgically prepared distal end 14 of a femur 16. The femoral component 12 includes an inferior articular bearing face defined by a pair of convex condyles 18 and 20 respectively.

The prosthesis 10 further includes a tibial component 22. The tibial component 22 is mounted to the resected proximal end 24 of the tibia 26 as shown in FIGS. 10–15. The tibial component 22 includes a generally conical extension 28 that is received in a cavity prepared in the resected proximal end 24 of the tibia 26. Additionally, the tibial component 22 includes an inferior bone engagement surface 30 substantially surrounding the conical extension. The conical extension 28 and the inferior bone engagement surface 30 may be coated or otherwise treated to ensure affixation to the tibia 26. Additionally or alternatively, the conical extension 28 and the inferior surface 30 of the tibial component 22 may include structural configurations for cooperating with bone cement to affix the tibial component 22 to the tibia 26.

Figure 9:
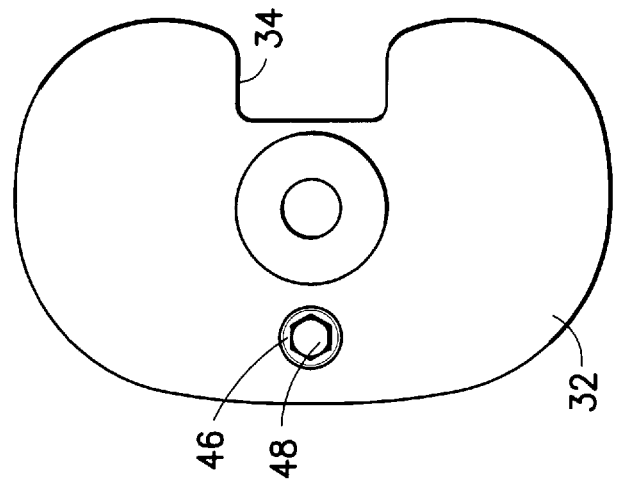
FIG. 9 is a top plan view of the tibial component of the subject invention.
Figure 7:
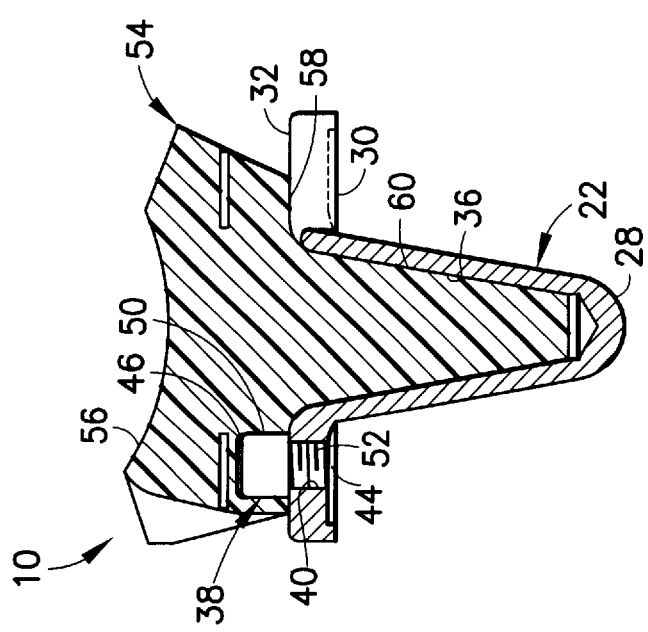
FIG. 7 is a cross-sectional view of a prosthesis in accordance with the subject invention.

As shown most clearly in FIGS. 7 and 9, the tibial component 22 includes a superior bearing surface 32 which, in the illustrated embodiment is substantially planar. The superior bearing surface 32 of the tibial component 22 defines a generally oval shape conforming to the size and shape of the resected end 24 of the tibia 26. The superior bearing surface 32 of the tibial component 22 includes a posterior notch 34 for accommodating the posterior cruciate ligament, if present. Central portions of the superior bearing surface 32 are characterized by a conical recess 36 that is formed in the conical extension 28 described above. The recess has an axis and will rotatably accommodate the bearing of the prosthetic joint 10 as explained further below.

The superior bearing face 32 of the tibial component 22 is further characterized by a stop 38 disposed between conical recess 36 and the anterior extreme of the superior bearing surface 32. As shown most clearly in FIG. 7, the stop 38 is attached removably to the tibial component 22. In particular, a threaded aperture 40 extends through the superior bearing face 32 of the tibial component 22 at a location anteriorly of the conical recess 36. The threaded aperture 40 is generated about an axis that extends parallel to the axis of the conical recess 36. The stop 38 includes proximal end 44 and a distal end 46. The proximal end 44 of the stop 38 is characterized by a non-circular recess 48 extending therein to accommodate a tool for threadedly engaging the stop 38 in the threaded recess 40 of the tibial component 22. Portions of the stop 38 extending distally from the proximal end 44 define a smooth cylindrical external surface 50. The stop 38 further includes an array of external threads 52 extending from the distal end 46 to the cylindrical surface 50. The threads 52 of the stop 38 are threadedly engaged in the threaded aperture 40 of the tibial component 22.

Figure 5:
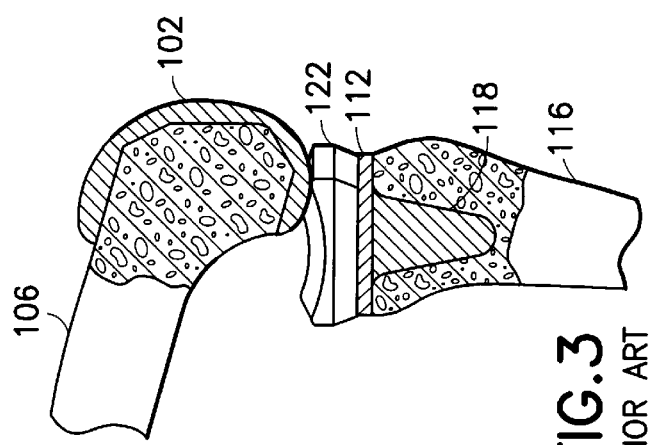
FIG. 5 is a cross-sectional view of the prior art prosthesis after dislocation due to spin-out.
Figure 3:
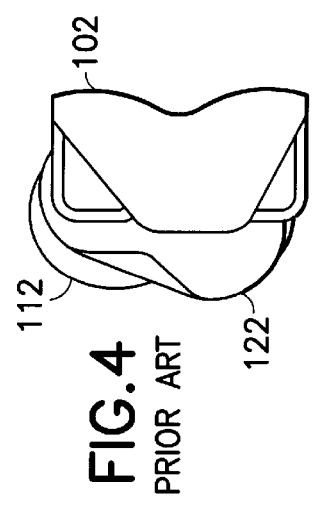
FIG. 3 is a cross-sectional view of the prior art prosthesis shown in FIG. 1, but showing a distracted condyle climbing over the bearing lip.
Figure 2:
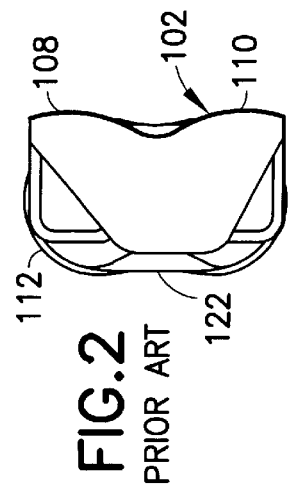
FIG. 2 is a top elevational view of the prior art prosthesis shown in the FIG. 1 position.
Figure 1:
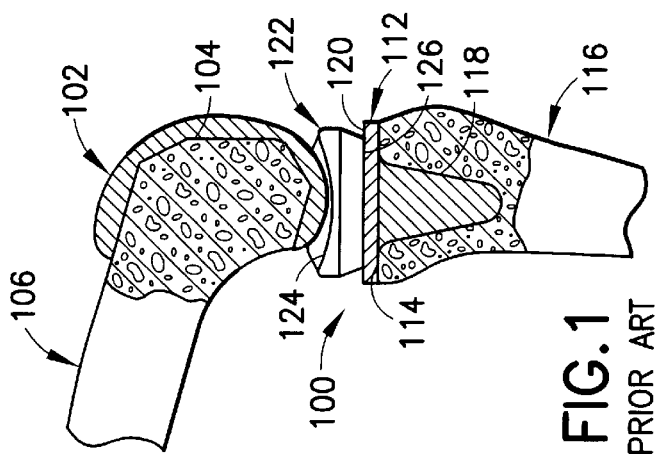
FIG. 1 is a cross-sectional view of a prior art prosthesis in a normal position.
Figure 8:
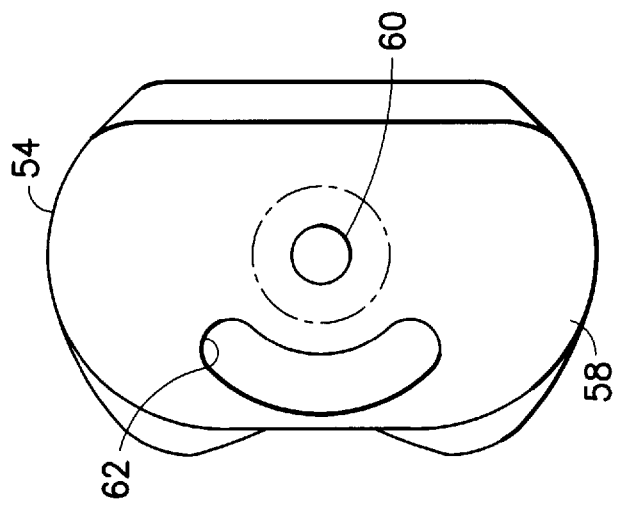
FIG. 8 is a bottom plan view of the bearing of the prosthesis of the subject invention.

The knee prosthesis 10 further includes a bearing 54 as shown most clearly in FIGS. 5 and 8. The bearing may be unitarily molded from a non-metallic material and includes a superior articular bearing surface 56 configured concavely for articular bearing engagement with the condyles 18 and 20 of the femoral component 12. The bearing 54 further includes a generally planar inferior bearing surface 58 and a conical projection 60 projecting distally from a central region of the inferior bearing surface 58. The conical projection 60 is dimensioned and configured to be retained rotatably in the recess 36 of the tibial component 22, while the inferior bearing surface 58 is in rotary bearing engagement with the superior bearing surface 32 of the tibial component 22.

Figure 11:
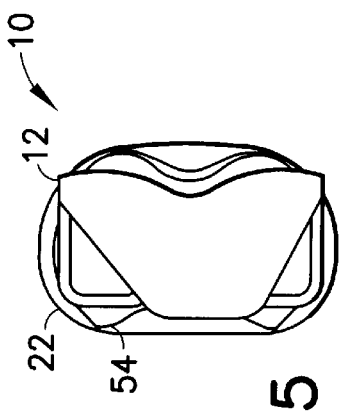
FIG. 11 is a top plan view of the prosthesis shown in FIG. 10.
Figure 13:
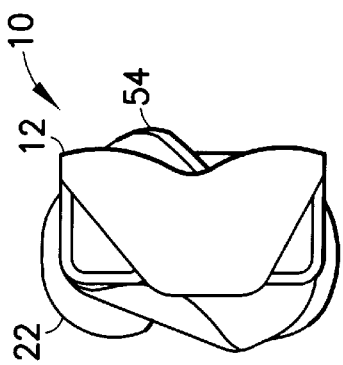
FIG. 13 is a top plan view of the prosthesis shown in FIG. 12.
Figure 15:
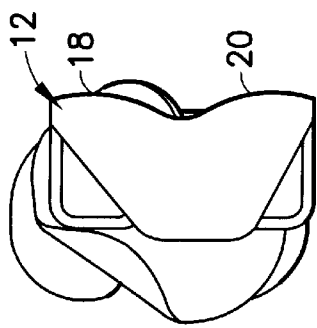
FIG. 15 is a top plan view of the prosthesis shown in FIG. 14.
Figure 10:
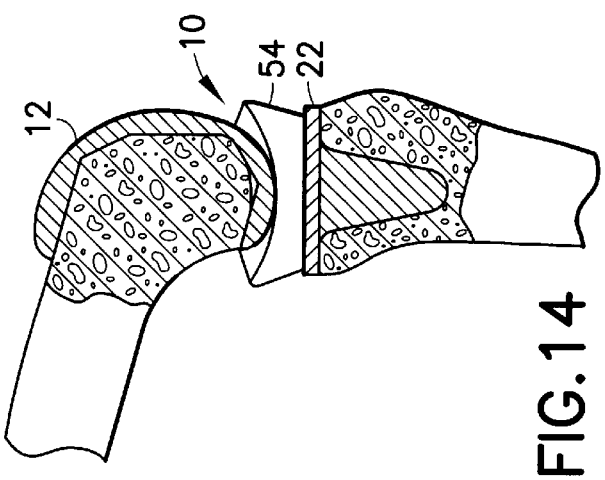
FIG. 10 is a cross-sectional view of the prosthesis of the subject invention with a distracted condyle climbing over the bearing lip.
Figure 12:
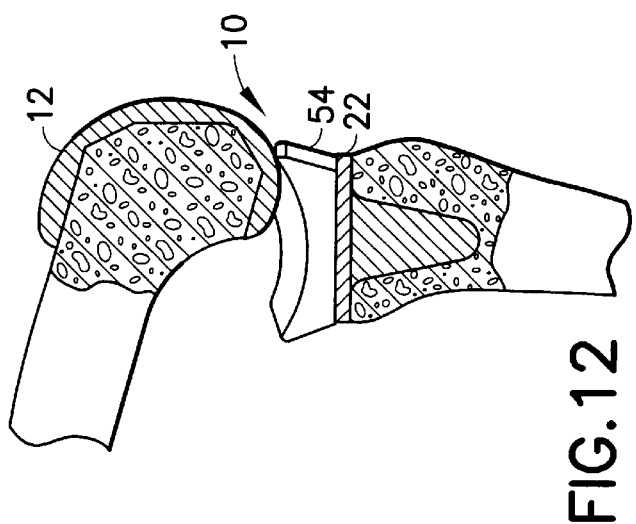
FIG. 12 is a cross-sectional view showing the prosthesis of the subject invention partially self-reduced.
Figure 14:
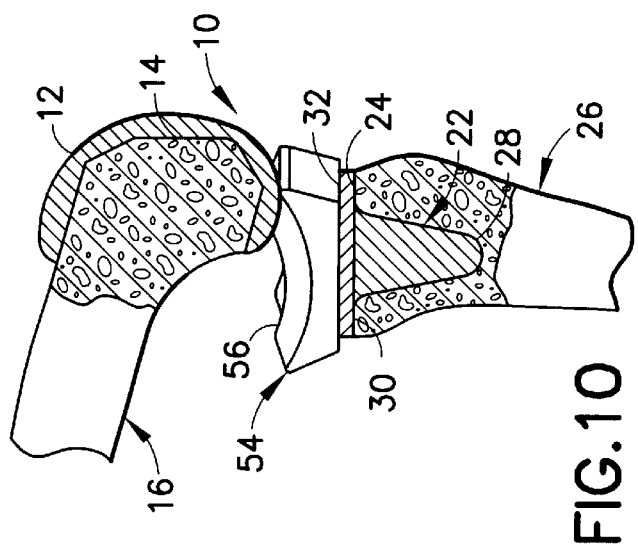
FIG. 14 is a cross-sectional view of the prosthesis of the subject invention in the normal position.

As shown most clearly in FIGS. 7 and 8, the inferior bearing surface 58 of the bearing 54 is characterized by an arcuate slot 62 disposed anteriorly of the conical projection 60 and generated concentrically about the axis of the conical projection 60. The slot 62 is dimensioned to slidably receive the cylindrical portion 50 of the stop 38. The slot 62 extends through an arc of proximally 90° and is symmetrical with respect to an anterior-posterior axis. Thus, the slot 62 and the projection 38 permit rotary motion of the bearing 54 about the axis of the conical projection 60 within a range of 45° in either direction of a normal position where the anterior-posterior axis of the bearing 54 aligns with the anterior-posterior axis of the tibial component 22. Thus, the knee prosthesis 10 permits axial rotation which is sufficiently in excess of a required maximum rotation of 80° (+/−40°) needed for most human activities, including deep knee flexion and associated large axial rotation. Thus, the combination of the stop 38 and the slot 62 do not affect normal knee functioning. As a result, the combination of the stop 38 and the slot 62 substantially prevents the above-described spinout problems. In particular, FIGS. 10 and 11 show a distracted condyle of the femoral component 12 with the bearing 54 spun sufficiently for an end of the slot 62 to engage the stop 38. In this position, the anterior lip of the bearing 54 is anterior to the center of the femoral condyle. Thus, when a compressive load is applied to the distracted condyle, this side of the bearing 54 will be forced anteriorly as shown in FIGS. 12 and 13 until the bearing has been forced into its normal position as shown in FIGS. 14 and 15.

FIG. 9 shows a posterior cruciate notch 34 formed in the tibial component 22. The notch 34 is provided to permit retention of the posterior cruciate ligament, which, as explained above, contributes to improved functioning of the knee and which provides stability for resisting dislocation. For such an application, a rotary stop is not needed and is undesirable. In these situations, the stop 38 need merely be threadedly removed from the aperture 40 in the tibial component 22 to permit use of the prosthesis 10 without a rotary stop.

What is claimed is:

1. A prosthetic joint comprising:
   a first component for secure affixation to a first bone of the joint, the first component having an articular bearing surface facing away from the first bone;
   a second component for affixation to a second bone of the joint, the second component having a rotary bearing surface facing away from the second bone and having a recess extending into the rotary bearing surface, said recess defining an axis; and
   a bearing having first bearing surface for articular bearing engagement with the first component and a second bearing surface for rotary bearing engagement with the bearing surface of the second component, the bearing further including a projection extending from the second bearing surface and rotatably engaged in the recess of the second component, the projection defining an axis concentric with the axis of the recess; wherein
   the rotary bearing surface of the second component being provided with a stop projecting therefrom and spaced from the concentric axes, and the second bearing surface of the bearing being formed with an arcuate slot concentric about the axes, said slot extending through a selected angle and slidably receiving said stop for limiting rotation of said bearing relative to said second component, said stop being removably engaged in the second component.

2. The prosthetic joint of claim 1, wherein the slot extends through an angle of approximately 90°.

3. The prosthetic joint of claim 1, wherein portions of the stop extending from the bearing surface of the second component are substantially cylindrical and define an axis substantially parallel to the axis of the recess in the second component.

4. The prosthetic joint of claim 1, wherein the second component includes a threaded aperture extending into the bearing surface, the stop including a threaded end removably engaged in the threaded aperture of the second component.

5. The prosthetic joint of claim 1, wherein the bearing surface of the second component is substantially planar at all locations spaced from the recess and spaced from the stop.

6. The prosthetic joint of claim 1, wherein the second bearing surface of the bearing is substantially planar at all locations thereon spaced from the projection and spaced from the slot.

7. The prosthetic joint of claim 1, wherein the joint is a knee joint, the first bone being a femur and the second bone being a tibia, the first component being a femoral component having a superior surface configured for engagement with the femur and having an inferior surface comprising a pair of condyles, the second component being a tibial component having an inferior surface configured for affixation to the tibia, the superior bearing surface of the bearing being configured for engaging the condyles of the femoral component in articular bearing engagement.

8. A knee joint prosthesis comprising:

a femoral component having a superior surface for affixation to a femur of the knee joint, the femoral component further comprising an inferior articular bearing surface defining a pair of condyles;

a tibial component having an inferior surface configured for affixation to a resected proximal end of a tibia of the knee joint, the tibial component further having a superior bearing surface, a recess extending into the superior bearing surface and defining an axis, a stop projecting proximally from the superior bearing surface at a location spaced from the recess, the stop being substantially parallel to the axis of the recess, said stop being removably engaged in the tibial component; and a bearing having a superior bearing surface in articular bearing engagement with the condyles of the femoral component, an inferior surface having a projection rotatably engaged in the recess of the tibial component for rotation about the axis thereof, portions of the inferior surface of the bearing spaced from the projection thereof defining an inferior bearing surface in rotary bearing engagement with the superior bearing surface of the tibial component, an arcuate slot being formed in the inferior bearing surface of the bearing and engaging the stop of the tibial component, the slot being substantially concentric with the axis and defining a selected arc such that engagement of said stop in said slot limits rotation of said bearing on said tibial component to an angular mount defined by the arc.

9. The knee joint prosthesis of claim 8, wherein the slot extends through an angle of approximately 90°.

10. The knee joint prosthesis of claim 8, wherein portions of the stop extending from the bearing surface of the tibial component are substantially cylindrical and define an axis substantially parallel to the axis of the recess in the tibial component.

11. The knee joint prosthesis of claim 8, wherein the tibial component includes a threaded aperture extending into the bearing surface, the stop including a threaded end removably engaged in the threaded aperture of the tibial component.

12. The knee joint prosthesis of claim 8, wherein the bearing surface of the tibial component is substantially planar at all locations spaced from the recess and spaced from the stop.

13. The knee joint prosthesis of claim 8, wherein the second bearing surface of the bearing is substantially planar at all locations thereon spaced from the projection and spaced from the slot.

* * * * *